US00PP19415P3

(12) United States Plant Patent
Ruter

(10) Patent No.: US PP19,415 P3
(45) Date of Patent: Nov. 4, 2008

(54) ***CAMPSIS* PLANT NAMED 'RUTCAM'**

(50) Latin Name: *Campsis xtagliabuana*
Varietal Denomination: RUTCAM

(75) Inventor: John M. Ruter, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 11/652,408

(22) Filed: Jan. 10, 2007

(65) Prior Publication Data

US 2008/0184410 P1 Jul. 31, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L. Bell
*Assistant Examiner*—June Hwu
(74) *Attorney, Agent, or Firm*—Greenlee Winner and Sullivan PC

(57) ABSTRACT

A new and distinct *Campsis xtagliabuana* hybrid which is characterized by a vine-like growth habit requiring support to grow, early flowering, and prolific blooming with red flowers.

2 Drawing Sheets

Figure 1:
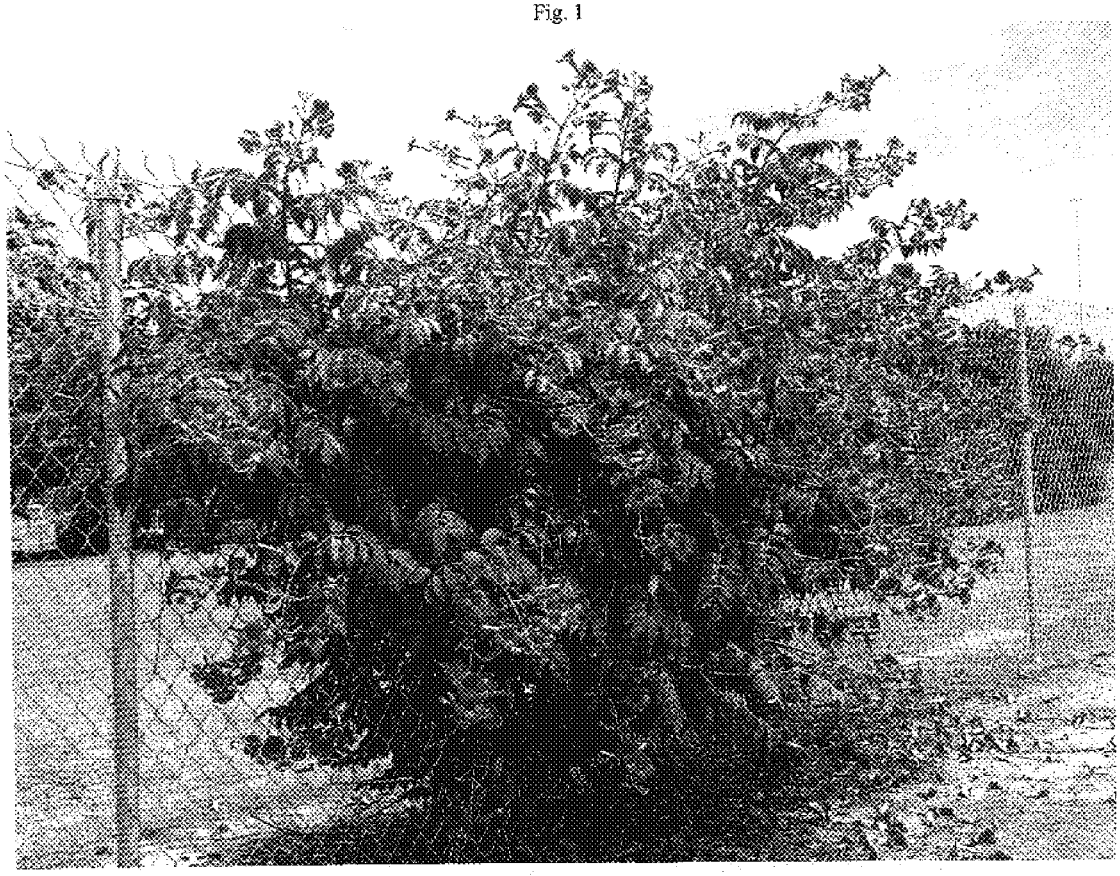

Botanical classification: *Campsis xtagliabuana.*
Varietal denomination: 'RUTCAM'.

BACKGROUND OF THE INVENTION

The present invention relates to a new and distinct cultivar of the ornamental vine, hereinafter referred to by the varietal denomination 'RUTCAM'. 'RUTCAM' was discovered growing on a fence in a garden in Tift County, Ga. in 1993. From its general morphological similarities to 'Madame Galen' a commercial cultivar (unpatented) of *Campsis xtagliabuana,* and from descriptions in the literature (Stearn, 1953; Sargent, 1905) the plant was identified as *Campsis xtagliabuana,* initially known as *Tecoma xtagliabuana,* a cross between trumpet vine, *Campsis radicans,* and chinese trumpet vine, *Campsis grandiflora* (also known as *Campsis chinensis*). Semi-hardwood cuttings were collected from that plant in June 1993 and plants so propagated have been grown and evaluated at Tifton for flowering and foliage characteristics, plant form, cold hardiness and drought tolerance. The original plant was destroyed when the garden and home site were destroyed.

'RUTCAM' is an attractive ornamental vine, requiring support to grow and flower profusely throughout the summer in landscape settings, with red orange flowers. It has been compared with *C.chinensis* 'Morning Calm' (unpatented) and *C. xtagliabuana* 'Madame Galen'. A plant growing on a fence in Tifton, Ga. (USDA Zone 8a) reached a height of 3.0 m with a spread of 4.0 m in 8 years. 'RUTCAM' comes into bloom 6 to 12 days before 'Morning Calm' and 9 days before 'Madame Galen'. The flower color of 'RUTCAM' is Red 46B compared to the Orange-Red 34A of 'Madame Galen' and the pink/pastel orange of 'Morning Calm'. 'RUTCAM' has more leaflets than 'Madame Galen', 12 compared to 10, and the leaf color is yellow green compared to the green of 'Madame Galen', with prominent abaxial leaf and rachis pubescence compared to the sparse pubescence of 'Madame Galen'. Under the conditions of growth in Tifton, Ga., 'RUTCAM' does not show the invasiveness of *C.radicans* by root sprouts or layering reported in the northeastern U.S.

SUMMARY OF THE INVENTION

Plants of 'RUTCAM' have not been observed under all possible environmental conditions. The phenotype may vary somewhat with variations in environment such as light-intensity, temperature and cultural conditions, however without any variance in genotype.

The following characteristics have been consistently observed and, to the best knowledge of the inventor, their combination forms the unique characteristics of 'RUTCAM' as a new and distinct cultivar.

1. Early flowering in late April to early May in side by side comparisons with 'Morning Calm' and 'Madame Galen'.
2. Large, red flowers compared to the orange-red of 'Madame Galen'.
3. Different leaf characteristics in terms of leaflet number, color and pubescences compared to 'Madame Galen'.

'RUTCAM' is readily propagated from 2 to 3 node sub-terminal cuttings throughout the growing season. Asexual propagation at Tifton, Ga. since 1999 has shown that the unique characteristics of this new cultivar are stable and reproduced true to type in successive generations.

BRIEF DESCRIPTION OF PHOTOGRAPHS

The accompanying colored photographs illustrate the characteristics of the new cultivar, showing the colors as true as it is reasonably possible to obtain in colored reproductions of this type. Colors in the photograph may differ from the color values listed in the detailed botanical description which accurately describes the colors of the new *campsis*.

FIG. 1. A 6-year old plant growing on fence in Tifton, Ga., taken Jun. 6, 2005.

Figure 2:
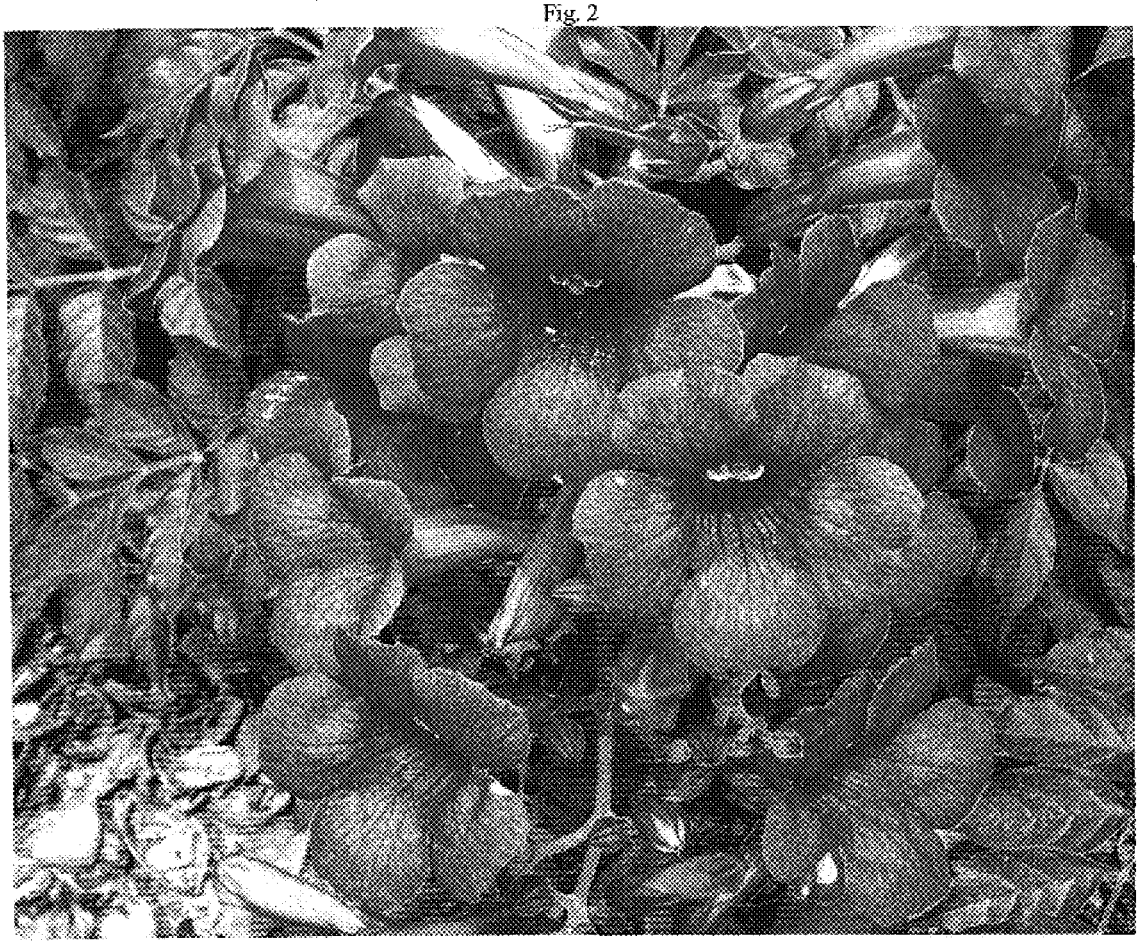

FIG. 2. Close up of flowers, taken May 6, 2002.

BOTANICAL DESCRIPTION OF THE PLANT

The botanical description of 'RUTCAM' is based on 8-year old plants growing on a fence in full sun in Tifton, Ga. (USDA Zone 8a). Colors are based on The Royal Horticultural Color Chart (2001). Unless otherwise indicated, measurements, based on 10 to 20 samples, were taken from May to September, 2006.

The plant is a woody, deciduous vine requiring support for maximum flower production, attaining an average height of 300 cm and spread of 400 cm after 8-years, fence supported growth in the field.

The leaves are opposite, petiolate, odd-pinnately compound. The average size of the leaf is between 30 cm and 35 cm. The mature leaf has 11–13 leaflets, the largest average 6.0 cm long by 3.0 cm wide. Leaflets are mostly ovate in shape with an acuminate apex, rounded base and serrate margin. The adaxial surface of the leaf is green 137A in color and sparsely pubescent. The abaxial surface is yellow-green 146B in color, with prominent short pubescence, especially on the midrib and lateral veins. The rachis is rounded on the abaxial side, curved to flat on the sides with a depression or groove on the adaxial surface, and is very finely pubescent. The rachis is green 138C in color.

New branch growth is pubescent, yellow green 144B in color. Old branch growth is slightly pubescent, grey orange 164C.

The petiole length is 0 to 9 mm. The petiole surface is very finely pubescent and green 138C.

The inflorescence is a cyme with up to 16 bisexual flowers, not all at anthesis at the same time. The inflorescence average size is approximately 30 cm across. The calyx is a leathery, cylindrical tube 2.5 cm in length with 5 triangular lobes, 11 to 13 mm in length, finely pubescent on the margins with mucronate tips, and Orange-Red 34B in color. The corolla is tubular-campanulate in shape and 6.5 cm in length. The narrow, cylindrical basal portion is 2.0 cm. long, gradually expanding to a swollen funnel 4.0 to 4.5 cm in length, the mouth being 3.0 cm across. The open flower is 7.0 cm across, consisting of 5 spreading, slightly curved lobes, 2.2 cm long and 2.7 cm across, with fine hairs on the margins. The interior of the funnel has numerous Red 46A lines, on a Yellow-Orange 16A background. The overall color of the flower is red 46B. The flowers bloom heavily in may and last sporadically until frost. Flower buds have a length of approximately 4 cm, a diameter of approximately 1.5 cm, are tubular in shape, and are yellow orange 21B.

The peduncle has a length of approximately 12 to 15 cm, and is yellow green N144D. The pedicel has a length of approximately 0.5 cm, and is yellow green N144D.

There are 5 stamens, 2 pairs of unequal length, 2.4 and 4.0 cm, and one reduced.

The anther is thecae divergent, 8 mm in length and Yellow 11B in color.

The filaments are curved, glabrous, inserted proximally within the corolla tube, not exserted.

The pollen color is Yellow 12C.

There is a single pistil with superior ovary, seated on a thick disc broader than its narrow base.

The stigma has 2 flat lobes, rounded in shape, and is Green-Yellow 1B in color.

The style is slender, 5 cm long and sparsely pubescent.

The fruit is a fusiform, bi-valved dehiscent capsule, keeled along sutures, 15 cm long and 1.5 cm wide. The color is Green 137C before drying and dehiscing. Few fruits are produced on plants grown in Tifton, Ga.

The seeds, many per fruit, are flat, 8.5 mm long by 6.5 mm wide, with conspicuous wings on either side, and Greyed-Orange 166A in color.

Pest problems have been minimal on field grown plants at Tifton, Ga., with some late season leaf spots.

What is claimed is:

1. A new and distinct and cultivar of *Campsis xtagliabuana* plant named 'RUTCAM', substantially as illustrated and described.

* * * * *